(12) United States Patent
Steber et al.

(10) Patent No.: US 6,552,002 B2
(45) Date of Patent: Apr. 22, 2003

(54) SUSTAINED-RELEASE COMPOSITIONS FOR PARENTERAL ADMINISTRATION

(75) Inventors: William David Steber, Ewing, NJ (US); Sivaja Ranjan, Princeton Junction, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/809,525

(22) Filed: Mar. 15, 2001

(65) Prior Publication Data

US 2002/0004486 A1 Jan. 10, 2002

Related U.S. Application Data

(60) Provisional application No. 60/190,699, filed on Mar. 20, 2000.

(51) Int. Cl.$^7$ .................................................. A61K 31/70
(52) U.S. Cl. .............................. 514/30; 514/27; 514/28
(58) Field of Search .............................. 514/30, 27, 28, 514/29; 424/78.08; 536/7.1

(56) References Cited

U.S. PATENT DOCUMENTS 4,389,397 A * 6/1983 Lo et al. ........................ 514/30

FOREIGN PATENT DOCUMENTS

| SA | 9708352 | 9/1997 |
|----|---------|--------|
| WO | WO 97/11709 | 4/1997 |
| WO | WO 98/11902 | 3/1998 |

* cited by examiner

*Primary Examiner*—Elli Peselev
(74) *Attorney, Agent, or Firm*—Joseph M. Mazzarese

(57) ABSTRACT

Sustained-release compositions comprising a macrolide compound, a surfactant, a co-solvent, and a solvent. The sustained-release compositions of this invention may be parenterally administered to animals, and are useful for preventing or treating helminth, acarid or arthropod endo- or ectoparasitic infection or infestation in warm-blooded animals for prolonged periods of time.

22 Claims, 1 Drawing Sheet

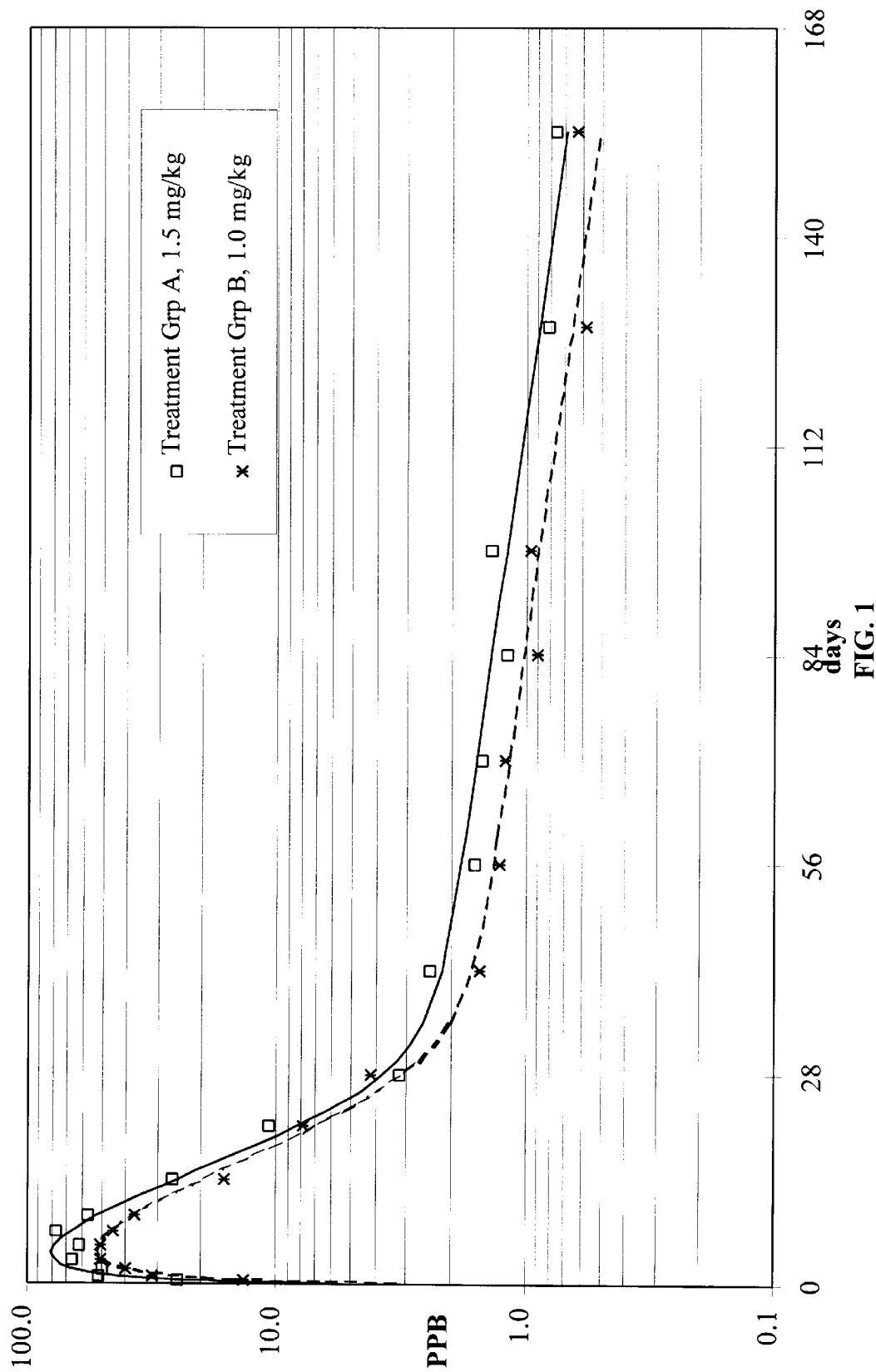

SUSTAINED-RELEASE COMPOSITIONS FOR PARENTERAL ADMINISTRATION

This application claims priority from copending provisional application(s) serial No. 60/190,699 filed on Mar. 20, 2000.

BACKGROUND OF THE INVENTION

Helminthiasis is a widespread disease found in many animals and is responsible for significant economic losses throughout the world. Among the helminths most frequently encountered are the group of worms referred to as nematodes. The nematodes are found in the gastrointestinal tract, heart, lungs, blood vessels and other body tissues of animals and are a primary cause of anemia, weight loss and malnutrition in the infected animals. They do serious damage to the walls and tissue of the organs in which they reside and, if left untreated, may result in death to the infected animals.

The nematodes most commonly found to be the infecting agents of ruminants include Haemonchus and Ostertagia generally found in the abomasum; Cooperia, Trichostrongylus and Nematodirus generally found in the intestinal tract, and Dictyocaulus found in the lungs. In non-ruminant animals important nematodes include Toxocara and Ancylostoma in the intestine and Dirofilaria in the heart of dogs and cats; Ascaridae in the intestine of swine; and large and small strongyles in equines.

Arthropod ectoparasites commonly infecting warm-blooded animals include ticks, mites, lice, fleas, blowfly, the ectoparasite Lucilia sp. of sheep, biting insects and migrating dipterous larvae such as Hypoderma sp. in cattle, Gastrophilus in horses and Cuterebra sp. in rodents.

Macrolide compounds such as LL-F28249$\alpha$-$\lambda$ compounds, 23-oxo or 23-imino derivatives of LL-F28249$\alpha$-$\lambda$ compounds, milbemycin compounds, avermectin compounds, and mixtures thereof are useful for the prevention and control of helminthiasis and infection by acarids and arthropod endo- and ectoparasites in warm-blooded animals. Parenteral injection of compositions is one of the preferred methods for administering those compounds.

To provide prolonged protection from helminth, acarid or arthropod endo- or ectoparasitic infection or infestation in warm-blooded animals it is desirable to use sustained-release injectable compositions having a relatively high loading of macrolide compounds. However, it is difficult to formulate injectable compositions containing a relatively high loading of macrolide compounds because macrolide compounds are, in general, poorly soluble in conventional solvents used in injectable compositions.

Injectable compositions containing macrolide compounds, vegetable oils and alcohols are described in WO 97/11709. However, that reference discloses that the macrolide compounds may be present in injectable compositions in an amount of only from 0.5% to 5% by weight.

South African Patent Application No. 9708352 discloses injectable macrolide compositions containing macrolide compounds; sesame oil; medium-chain triglycerides or glycol esters or fatty acid esters; and aliphatic or aromatic mono- or polyhydric alcohols and their derivatives or castor oil. However, the injectable compositions described in this reference contain only from 0.2% to 5% w/v of the macrolide compounds.

It is an object of the present invention to provide a sustained-release composition for parenteral administration which comprises a relatively high loading of macrolide compounds.

It is also an object of the present invention to provide a method for preventing or treating helminth, acarid or arthropod endo- or ectoparasitic infection or infestation in warm-blooded animals for prolonged periods of time.

It is another object of this invention to reduce or control the proliferation of helminths, nematodes and parasites in warm blooded animals for prolonged periods of time.

These and other objects of the present invention will become more apparent from the description thereof set forth below and the appended claims.

SUMMARY OF THE INVENTION

The present invention provides sustained-release compositions for parenteral administration which comprise on a weight to volume basis: about 5% to 30% of a macrolide compound or mixture of macrolide compounds; about 1% to 10% of a low-HLB surfactant or mixture of low-HLB surfactants; about 1% to 20% of a co-solvent selected from the group consisting of an aromatic alcohol, a cyclic amide and mixtures thereof; and a solvent selected from the group consisting of triglycerides of medium chain fatty acids, glycol esters of medium chain fatty acids and mixtures thereof.

The present invention further provides a method for preventing or treating helminth, acarid or arthropod endo- or ectoparasitic infection or infestation in a warm-blooded animal which method comprises parenterally administering to the animal an anthelmintically, acaricidally or arthropod endo- or ectoparasiticidally effective amount of the composition of this invention.

BRIEF DESCRIPTION OF THE DRAWING

FIG. 1 is a graph depicting the blood concentration profile of moxidectin in calves treated with composition number 2.

DETAILED DESCRIPTION OF THE INVENTION

In accordance with the present invention, the sustained-release compositions comprise a macrolide compound; a low-HLB surfactant; a co-solvent selected from the group consisting of an aromatic alcohol and a cyclic amide and mixtures thereof; and a solvent selected from the group consisting of triglycerides of medium chain fatty acids and glycol esters of medium chain fatty acids and mixtures thereof. The invention also provides a method for preventing or treating helminth, acarid or arthropod endo- or ectoparasitic infection or infestation in warm-blooded animals.

Preferred sustained-release compositions of this invention comprise on a weight to volume basis about 10% to 20% of the macrolide compound or mixture of macrolide compounds; about 1% to 10% of the low-HLB surfactant or mixture of low-HLB surfactants; about 1% to 15% of the co-solvent; and the solvent.

Uniquely, it has been found that sustained-release compositions having relatively high loadings of macrolide compounds may be obtained when a low-HLB surfactant is used in combination with the co-solvent and solvent of the present invention. Advantageously, the rate of absorption of macrolide compounds from subcutaneous injection depots is controlled through the inventive combination of a low-HLB surfactant, co-solvent and solvent to achieve: (1) long lasting therapeutic efficacy; (2) relatively low peak blood levels; and (3) essentially complete absorption. Long lasting efficacy is advantageous because animals will need to be treated less frequently. By providing relatively low peak blood levels, the inventive compositions reduce the risk of systemic toxicity associated with high blood levels of certain macrolide compounds. Essentially complete absorption is highly desirable because it reduces the risk of unacceptable injection site irritation, and minimizes injection site and/or tissue residues.

The term "low-HLB surfactant" as used in the specification and claims refers to a surfactant that has a hydrophilic/lipophilic balance of about 1 to 9, preferably about 2 to 7. Low-HLB surfactants suitable for use in the compositions of this invention include, but are not limited to, sorbitan esters such as sorbitan monooleate, sorbitan stearate, sorbitan laurate, sorbitan trioleate, sorbitan sesquioleate, and the like; and glycerol esters such as glyceryl monolaurate, glycerol monooleate, and the like. A preferred low-HLB surfactant is sorbitan monooleate which is commercially available under a variety of tradenames including, but not limited to, CRILL® 4 (Croda Inc., Parsippany, N.J.), LIPOSORB® O (Lipo Chemicals Inc., Paterson, N.J.), and LIPOSORB® L (Lipo Chemicals Inc.).

Aromatic alcohols suitable for use in the present invention include, but are not limited to, benzyl alcohol, α-ethylbenzyl alcohol, phenethyl alcohol and the like and mixtures thereof. Cyclic amides which may be used in the compositions of this invention include, but are not limited to, 1-methyl-2-pyrrolidinone (NMP) and the like. Preferred co-solvents include benzyl alcohol and 1-methyl-2-pyrrolidinone and mixtures thereof.

Triglycerides of medium chain fatty acids suitable for use in the compositions of this invention include, but are not limited to, triglycerides of $C_6$–$C_{14}$ fatty acids such as triglycerides of caproic, caprylic, capric, lauric and/or myristic acids and the like and mixtures thereof. Preferred triglycerides of medium chain fatty acids include mixtures of triglycerides of caprylic and capric acids and are available under a variety of tradenames including, but not limited to, MIGLYOL® 810 and MIGLYOL® 812 (both commercially available from Creanova Inc., Somerset, N.J.).

Glycol esters of medium chain fatty acids useful in the sustained-release compositions of this invention include, but are not limited to, glycol esters of $C_6$–$C_{14}$ fatty acids such as glycol esters of caproic, caprylic, capric, lauric and/or myristic acids and the like and mixtures thereof. Preferred glycol esters of medium chain fatty acids include mixtures of propylene glycol diesters of caprylic and capric acids and are available under a variety of tradenames including, but not limited to, MIGLYOL® 840 (commercially available from Creanova Inc.). In a preferred embodiment of the present invention, the solvent comprises propylene glycol diesters of caprylic and capric acids.

Macrolide compounds useful in the compositions of this invention include, but are not limited to, LL-F28249α-λ compounds, 23-oxo or 23-imino derivatives of LL-F28249α-λ compounds, milbemycin compounds and avermectin compounds and mixtures thereof. The macrolide compounds include, but are not limited to, those described in U.S. Pat. Nos. 4,886,828; 5,019,589; 5,030,650; 5,055,486 and 5,108,992 incorporated herein by reference.

Preferred macrolide compounds include the compounds designated LL-F28249α-λ which are (collectively) isolates from the fermentation broth of the microorganism *Streptomyces cyaneogriseus* subspecies *noncyanogenus*, deposited in the NRRL under deposit accession No. 15773. The method for preparation of LL-F28249α is disclosed in U.S. Pat. No. 5,106,994 and its continuation, U.S. Pat. No. 5,169,956, incorporated herein by reference.

The LL-F28249α-λ compounds are represented by the following structural formula:

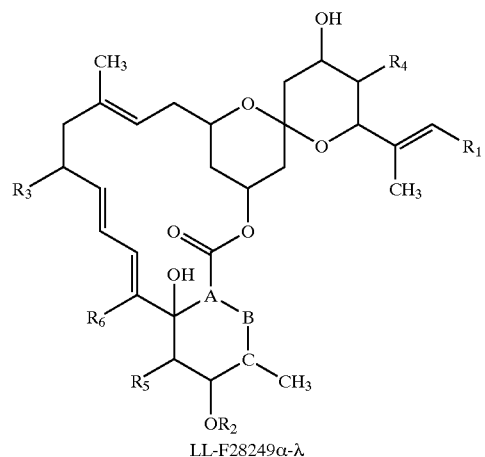

LL-F28249α-λ

The 23-oxo and 23-imino derivatives of LL-F28249α-λ compounds, useful in the compositions of this invention, are disclosed in U.S. Pat. No. 4,916,154, incorporated herein by reference, and in Table I.

TABLE I

| LL-F28249 | $R_1$ | $R_2$ | $R_3$ | $R_4$ | $R_5$ | $R_6$ | $R_5 + R_6$ | A–B | B–C |
|---|---|---|---|---|---|---|---|---|---|
| Alpha | $CH(CH_3)_2$ | H | $CH_3$ | $CH_3$ | | | —O—$CH_2$— | CH—CH | CH=C |
| Beta | $CH_3$ | H | $CH_3$ | $CH_3$ | | | —O—$CH_2$— | CH—CH | CH=C |
| Gamma | $CH_3$ | $CH_3$ | $CH_3$ | $CH_3$ | | | —O—$CH_2$— | CH—CH | CH=C |
| Delta | $CH_3$ | $CH_3$ | $CH_3$ | $CH_3$ | OH | $CH_2OH$ | | CH—CH | CH=C |
| Epsilon | $CH(CH_3)_2$ | H | H | $CH_3$ | | | —O—$CH_2$— | CH—CH | CH=C |
| Zeta | $CH_2CH_3$ | H | $CH_3$ | $CH_3$ | | | —O—$CH_2$— | CH—CH | CH=C |
| Eta | $CH(CH_3)_2$ | H | $CH_3$ | $CH_3$ | | | —O—$CH_2$— | C=CH | CH—CH |
| theta | $CH(CH_3)_2$ | H | $CH_3$ | $CH_2CH_3$ | | | —O—$CH_2$— | CH—CH | CH=C |
| iota | $CH(CH_3)_2$ | H | $CH_2CH_3$ | $CH_3$ | | | —O—$CH_2$— | CH—CH | CH=C |
| kappa | $CH_3$ | $CH_3$ | $CH_3$ | $CH_3$ | H | $CH_3$ | | CH—CH | CH=C |
| lambda | $CH(CH_3)_2$ | $CH_3$ | $CH_3$ | $CH_3$ | | | —O—$CH_2$— | CH—CH | CH=C |

A preferred LL-F28249α-λ compound and 23-imino derivative of an LL-F28249α-λ compound useful in the compositions of this invention have the following structural formulas:

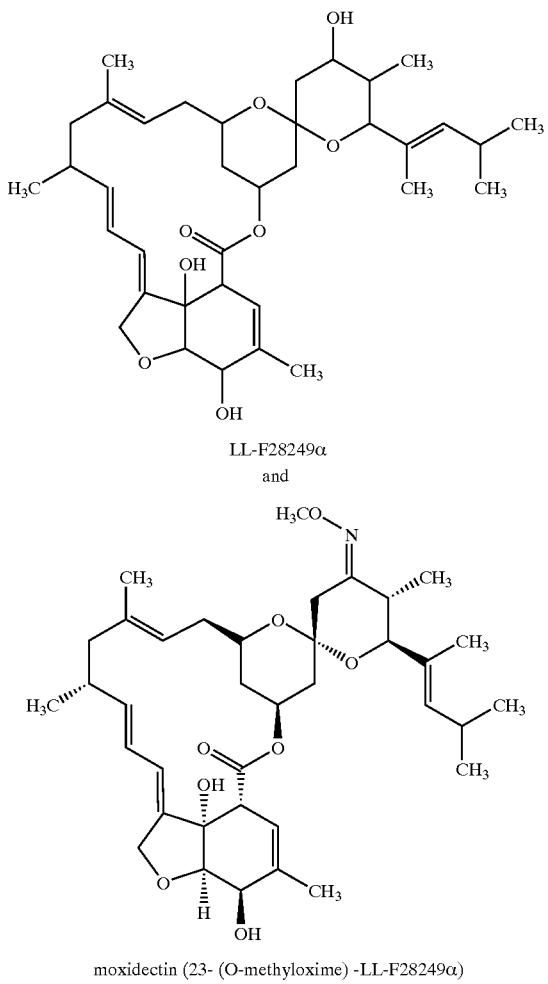

LL-F28249α
and moxidectin (23-(O-methyloxime)-LL-F28249α)

Milbemycin compounds suitable for use in the compositions of this invention include, but are not limited to, milbemycin D, milbemycin oxime and those compounds described in U.S. Pat. Nos. 3,950,360; 4,346,171 and 4,547,520, incorporated herein by reference. Preferred milbemycin compounds for use in this invention are milbemycin D and milbemycin oxime.

Avermectin compounds which are suitable for use in the invention compositions include, but are not limited to, abamectin, ivermectin, doramectin, eprinomectin, selamectin and those compounds described in U.S. Pat. Nos. 4,199,569 and 4,310,519, incorporated herein by reference, with ivermectin, abamectin, doramectin, eprinomectin and selamectin being preferred. Doramectin and a method for its preparation are described in U.S. Pat. No. 5,089,480, incorporated herein by reference.

An especially preferred sustained-release composition for parenteral administration to warm-blooded animals comprises, on a weight to volume basis, about 10% to 20% moxidectin; about 1% to 8% of sorbitan ester(s), preferably sorbitan monooleate; about 1% to 12% aromatic alcohol, preferably benzyl alcohol; and a solvent comprising propylene glycol diesters of caprylic and capric acids.

The compositions of this invention may further comprise other agents known in the art, such as preservatives (e.g., methylparaben and propylparaben), colorants, antioxidants, and the like. Generally, these agents would be present in the compositions in an amount up to about 2% on a weight to volume basis.

The compositions of the present invention may be prepared by admixing a mixture of the macrolide compound; the low-HLB surfactant; the co-solvent; and the solvent. A preferred preparation method comprises: (1) admixing a mixture of the low-HLB surfactant; the co-solvent; and the solvent to obtain a solution; and (2) admixing the macrolide compound with the solution.

When parenterally administered, the compositions of this invention are highly effective for preventing or treating helminth, acarid and arthropod endo- and ectoparasitic infection and infestation for prolonged periods of time in warm-blooded animals such as cows, sheep, horses, camels, deer, swine, goats, dogs, cats, birds, and the like.

In order to facilitate a further understanding of the invention, the following examples are presented primarily for the purpose of illustrating specific embodiments thereof. The invention is not to be deemed limited thereby, except as defined in the claims.

EXAMPLE 1
Preparation of Moxidectin Sustained-release Compositions

A solution of a sorbitan monooleate (4.2 g, CRILL® 4, commercially available from Croda Inc., Parsippany, N.J.), a propylene glycol diester of capric/caprylic acids—MIGLYOL® 840 (71.1 g, commercially available from Creanova Inc., Somerset, N.J.), and benzyl alcohol (7.3 g) is stirred at 50–60° C., treated portionwise with moxidectin (17.3 g, 90% real), stirred until the moxidectin dissolves, cooled to room temperature, and filtered to give the moxidectin sustained-release composition identified as composition number 1 in Table II.

Using essentially the same procedure, the moxidectin sustained-release compositions identified as composition numbers 2–9 in Table II are obtained.

TABLE II

Moxidectin Sustained-Release Compositions Ingredient/% w/v

| Composition Number | Moxidectin (theory) | Surfactant[1] | Primary Solvent[2] | Benzyl Alcohol | NMP[3] |
|---|---|---|---|---|---|
| 1 | 15 | A/4.0 | A/68.1 | 7.0 | — |
| 2 | 14.8 | B/3.9 | A/73.0 | 1.9 | — |
| 3 | 14.9 | B/8.1 | A/56.1 | 1.9 | 14.5 |
| 4 | 14.9 | C/8.0 | A/56.2 | 1.9 | 14.5 |
| 5 | 15.2 | B/4.0 | B/74.4 | 1.9 | — |
| 6 | 15.2 | B/4.1 | B/62.8 | 14.7 | — |
| 7 | 15.2 | B/4.1 | B/60.8 | 2.0 | 14.7 |
| 8 | 20.3 | C/7.6 | B/52.0 | 2.0 | 14.8 |
| 9 | 10 | A/4.0 | A/73.4 | 7.0 | — |

[1]A = CRILL® 4; B = LIPOSORB® O; C = LIPOSORB® L.
[2]A = MIGLYOL® 840; B = MIGLYOL® 812.
[3]NMP = 1-methyl-2-pyrrolidinone.

EXAMPLE 2
Evaluation of Moxidectin Sustained-release Compositions Against Intestinal Nematode Parasites Holstein calves are appropriately blocked with regard to weight and sex prior to random assignment to treatment groups. The calves are dosed with one of two dosages of composition 2 from Table II or are untreated. Thus, there are two treatment groups, plus an untreated control group. The calves are dosed at 133, 91, or 35 days prior to experimental infection with *Ostertagia ostertagi* and *Cooperia oncophora*, nematode parasites. Calves are injected with the compositions in the subcutaneous tissue of the external pinnae of the ear. Blood samples are taken from all animals for analysis of moxidectin concentrations in serum on selected days between 0 and 154 days after dosing. Calves are necropsied approximately 22 days after experimental infection, and the abomasum and small intestines are removed, processed and worms counted.

Treatment groups are as follows:

| Treatment Group | Composition Number[1] | Moxidectin Dose (mg/kg) |
|---|---|---|
| A | 2 | 1.5 |
| B | 2 | 1.0 |

[1]From Table II of Example 1.

Table III, shown below, summarizes the efficacy of composition 2 at two dosages (1.5 and 1.0 mg/kg of body weight) to prevent infection from *O. ostertagi* and *C. oncophora*. Infection from *O. ostertagi* is prevented at 35, 91, and 133 days after dosing; efficacy is nearly 100% at both dose levels. Thus, long term efficacy against this pathogenic organism is clearly demonstrated. Infection from *C. oncophora* is not prevented at any of the test times. However, this organism is known to be relatively insensitive to macrolide compounds including moxidectin.

The blood concentration profile of moxidectin in time in treated animals—as shown in FIG. 1—demonstrates the unique and surprising features of the compositions of the invention. These features include: delayed absorption; relatively low peak blood concentration; and long terminal elimination phase.

TABLE III

Efficacy Against *O. ostertagi* and *C. Onchophora*

| Group[a] | Composition Number | Dose (mg/kg) | Treatment Day Preinfection | % Efficacy O. ostertagi | C. oncophora |
|---|---|---|---|---|---|
| A1 | 2 | 1.5 | −133 | 99.8 | 0 |
| A2 | 2 | 1.5 | −91 | 99.9 | 0 |
| A3 | 2 | 1.5 | −35 | 98.8 | 0 |
| B1 | 2 | 1.0 | −133 | 97.6 | 0 |
| B2 | 2 | 1.0 | −91 | 99.9 | 0 |
| B3 | 2 | 1.0 | −35 | 99.7 | 0 |

[a]Five animals per group, 82 to 122 kg b.w. at Day −133.

What is claimed is:

1. A non-aqueous sustained-release macrolide composition for parenteral administration which comprises on a weight to volume basis about 5% to 30% of a macrolide compound or mixture of macrolide compounds; about 1% to 10% of a low-HLB surfactant having an HLB of about 1 to 9 or mixture of such low-HLB surfactants; about 1% to 20% of a co-solvent selected from the group consisting of an aromatic alcohol, a cyclic amide, and mixtures thereof; and a solvent selected from the group consisting of triglycerides of medium chain fatty acids, glycol esters of medium chain fatty acids, and mixtures thereof.

2. The composition according to claim 1 which comprises about 10% to 20% of the macrolide compound or mixture of macrolide compounds; about 1% to 10% of the low-HLB surfactant or mixture of low-HLB surfactants; and about 1% to 15% of the co-solvent.

3. The composition according to claim 1 wherein the macrolide compound is selected from the group consisting of an LL-F28249α-λ, a 23-oxo or 23-imino derivative of an LL-F28249α-λ, a milbemycin and an avermectin and mixtures thereof.

4. The composition according to claim 1 wherein the macrolide compound is selected from the group consisting of LL-F28249α, moxidectin, milbemycin D, milbemycin oxime, ivermectin, abamectin, doramectin, eprinomectin and selamectin.

5. The composition according to claim 4 wherein the macrolide compound is moxidectin.

6. The composition according to claim 1 wherein the aromatic alcohol is selected from the group consisting of benzyl alcohol, α-ethylbenzyl alcohol, phenethyl alcohol and mixtures thereof; and the cyclic amide is 1-methyl-2-pyrrolidinone.

7. The composition according to claim 1 wherein the co-solvent comprises benzyl alcohol.

8. The composition according to claim 1 wherein the triglycerides of medium chain fatty acids are triglycerides of $C_6$–$C_{14}$ fatty acids; and the glycol esters of medium chain fatty acids are glycol esters of $C_6$–$C_{14}$ fatty acids.

9. The composition according to claim 8 wherein the triglycerides of medium chain fatty acids comprise triglycerides of caprylic and capric acids; and the glycol esters of medium chain fatty acids comprise propylene glycol diesters of caprylic and capric acids.

10. The composition according to claim 1 wherein the low-HLB surfactant is selected from the group consisting of a sorbitan ester, a glycerol ester, and mixtures thereof.

11. The composition according to claim 10 wherein the low-HLB surfactant is selected from the group consisting of sorbitan monooleate, sorbitan stearate, sorbitan laurate, and mixtures thereof.

12. The composition according to claim 11 wherein the low-HLB surfactant is sorbitan monooleate.

13. The composition according to claim 1 which comprises about 10% to 20% moxidectin; about 1% to 8% sorbitan monooleate; about 1% to 12% benzyl alcohol; and a solvent comprising propylene glycol diesters of caprylic and capric acids.

14. The composition according to claim 1 wherein the macrolide compound is moxidectin; the low-HLB surfactant is selected from the gorups consisting of a sorbitan ester, a glycerol ester, and mixtures thereof; and the co-solvent comprises benzyl alcohol.

15. A method for preventing or treating helminth, acarid or arthropod endo- or ectoparasitic infection or infestation in a warm-blooded animal which method comprises parenterally administering to the animal an anthelmintically, acaricidally or arthropod endo- or ectoparasiticidally effective amount of a composition according to claim 1.

16. The method according to claim 15 wherein the animal is selected from the group consisting of a cow, a sheep, a horse, a camel, a deer, a swine, a goat, a dog, a cat, and a bird.

17. The method according to claim 15 wherein the composition comprises about 10% to 20% of the macrolide compound or mixture of macrolide compounds; about 1% to 10% of the low-HLB surfactant or mixture of low-HLB surfactants; about 1% to 15% of the co-solvent; and the solvent.

18. The method according to claim 15 wherein the macrolide compound is selected from the group consisting of LL-F28249α, moxidectin, milbemycin D, milbemycin oxime, ivermectin, abamectin, doramectin, eprinomectin and selamectin.

19. The method according to claim 18 wherein the macrolide compound is moxidectin.

20. The method according to claim 15 wherein the low-HLB surfactant is selected from the group consisting of a sorbitan ester and a glycerol ester and mixtures thereof; the aromatic alcohol is selected from the group consisting of benzyl alcohol, α-ethylbenzyl alcohol, phenethyl alcohol and mixtures thereof; the cyclic amide is 1-methyl-2-pyrrolidinone; the triglycerides of medium chain fatty acids are triglycerides of $C_6$–$C_{14}$ fatty acids; and the glycol esters of medium chain fatty acids are glycol esters of $C_6$–$C_{14}$ fatty acids.

21. The method according to claim 15 wherein the low-HLB surfactant is sorbitan monooleate; the co-solvent is benzyl alcohol; and the solvent comprises propylene glycol diesters of caprylic and capric acids.

22. The method according to claim 15 wherein the composition comprises about 10% to 20% moxidectin; about 1% to 8% sorbitan monooleate; about 1% to 12% benzyl alcohol; and a solvent comprising propylene glycol diesters of caprylic and capric acids.

* * * * *